United States Patent
Band et al.

(10) Patent No.: US 9,850,313 B2
(45) Date of Patent: Dec. 26, 2017

(54) CANCER BIOMARKERS AND METHODS OF USE THEREOF

(71) Applicant: The Board of Regents of the University of Nebraska, Lincoln, NE (US)

(72) Inventors: Vimla Band, Omaha, NE (US); Hamid Band, Omaha, NE (US); Sameer Mirza, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 14/416,502

(22) PCT Filed: Aug. 5, 2013

(86) PCT No.: PCT/US2013/053584
§ 371 (c)(1),
(2) Date: Jan. 22, 2015

(87) PCT Pub. No.: WO2014/022846
PCT Pub. Date: Feb. 6, 2014

(65) Prior Publication Data
US 2015/0203588 A1 Jul. 23, 2015

Related U.S. Application Data

(60) Provisional application No. 61/679,312, filed on Aug. 3, 2012.

(51) Int. Cl.
| | |
|---|---|
| *C07K 16/30* | (2006.01) |
| *G01N 33/574* | (2006.01) |
| *A61K 39/395* | (2006.01) |
| *A61K 45/06* | (2006.01) |
| *A61N 5/00* | (2006.01) |

(52) U.S. Cl.
CPC .... *C07K 16/3015* (2013.01); *A61K 39/39558* (2013.01); *A61K 45/06* (2013.01); *G01N 33/57415* (2013.01); *A61N 5/00* (2013.01); *G01N 2333/71* (2013.01); *G01N 2333/723* (2013.01); *G01N 2500/10* (2013.01); *G01N 2800/52* (2013.01)

(58) Field of Classification Search
CPC ............... G01N 33/53; G01N 33/574; G01N 33/57415; G01N 33/57484; G01N 33/57492; G01N 33/57496; G01N 33/576
See application file for complete search history.

(56) References Cited

U.S. PATENT DOCUMENTS

| | | |
|---|---|---|
| 2002/0072076 A1 | 6/2002 | Sakamoto et al. |
| 2005/0208500 A1 | 9/2005 | Erlander et al. |
| 2010/0120039 A1 | 5/2010 | Fuqua |
| 2011/0195995 A1 | 8/2011 | Wittliff et al. |

OTHER PUBLICATIONS

Meng, G., et al., The Journal of Biological Chemistry, 279(52): 54230-54240, 2004.*
Goldhirsch, A., et al., Annals of Oncology, Jun. 27, 2011, doi:10/1093/annonc/mdr304.*
McInnes, C., Drug Discovery Today, 13(19/20): 875-881, 2008.*
Mirza, S., et al., "Cytoplasmic Localization of Alteration/Deficiency in Activation 3 (ADA3) Predicts Poor Clinical Outcome in Breast Cancer Patients," Breast Cancer Res. Treat. (2013) 137:721-731.
Germaniuk-Kurowska, A., et al., "Ada3 Requirement for HAT Recruitment to Estrogen Receptors and Estrogen-Dependent Breast Cancer Cell Proliferation," Cancer Res. (2007) 67:11789-11797.
Mohibi, S., et al., "Mammalian Alteration/Deficiency in Activation 3 (Ada3) is Essential for Embryonic Development and Cell Cycle Progression," J. Biol. Chem. (2012) 287:29442-29456.
Nag, A., et al., "An Essential Role of Human Ada3 in p53 Acetylation," J. Biol. Chem. (2007) 282:8812-882.
Zeng, M., et al., "Human Papilloma Virus 16 E6 Oncoprotein Inhibits Retinoic X Receptor-mediated Transactivation by Targeting Human ADA3 Coactivator," J. Biol. Chrem. (2002) 277:45611-45618.
Collins, D.C., Bidirectional Receptor Crosstalk in Breast Cancer: the Role of c-myc and Coregulatory Proteins and Future Implications for Cancer Treatment, Ph.D. Thesis, 2010, Royal College of Surgeons in Ireland, available at http://epubs.rcsi.ie/cgi/viewcontent.cgi?article=1007&context=phdtheses.
Griffin, N.I., et al., "ADA3 regulates normal and tumor mammary epithelial cell proliferation through c-MYC" Breeast Cancer Res. (2016) 18:113.

* cited by examiner

*Primary Examiner* — Misook Yu
*Assistant Examiner* — Anne Holleran
(74) *Attorney, Agent, or Firm* — Robert C. Netter, Jr.; Dann, Dorfman, Herrell & Skillman (57) ABSTRACT

Methods and compositions for treating cancer, particularly breast cancer, are disclosed.

12 Claims, 8 Drawing Sheets

Figure 3

CANCER BIOMARKERS AND METHODS OF USE THEREOF

This application is a §371 application of PCT/US2013/053584, filed Aug. 5, 2013, which claims priority under 35 U.S.C. §119(e) to U.S. Provisional Patent Application No. 61/679,312, filed on Aug. 3, 2012. The foregoing applications are incorporated by reference herein.

This invention was made with government support under Grant No. 5R01 CA096844 awarded by the National Institutes of Health. The government has certain rights in the invention.

FIELD OF THE INVENTION

The present invention relates to the fields of cancer. More specifically, the invention provides compositions and methods for the identification and diagnosis of cancer, particularly breast cancer.

BACKGROUND OF THE INVENTION

Several publications and patent documents are cited throughout the specification in order to describe the state of the art to which this invention pertains. Each of these citations is incorporated herein by reference as though set forth in full.

With an estimated 230,480 new cases in the year 2011, and 39,520 of them fatal, breast cancer remains the most common malignancy and the second leading cause of cancer-related deaths among women in the U.S. (Jemal et al. (2011) CA Cancer J. Clin., 61:69-90). A combination of markers based on breast cancer pathogenesis has led to the classification of breast cancers into different subtypes that are associated with distinct patient outcomes. Thus, estrogen receptor (ER) and progesterone receptor (PR) positive (ER+/PR+) luminal type of breast cancers are amenable to hormonal therapy and show a substantially better outcome (Sorlie et al. (2001) Proc. Natl. Acad. Sci., 98:10869-10874). In contrast, human epidermal growth factor receptor 2 (HER2)/ErbB2-overexpressing and typically ER/PR-negative luminal breast cancers fail to respond to hormonal therapy and show substantially poorer outcomes compared to ER+/PR+ patients. This subtype of patients, however, selectively benefit from ErbB2-directed targeted therapies such as trastuzumab (Hudis, C. A. (2007) N. Engl. J. Med., 357:39-51).

There is a well-accepted role of the hormonal history of a woman as a determinant of her lifetime risk of developing breast cancer (Colditz, G. A. (1998) J. Natl. Cancer Inst., 90:814-823), a well-established pro-oncogenic role of estrogens in animal models (Korach et al. (2003) J. Steroid Biochem. Mol. Biol., 86:387-391; Mohibi et al. (2011) J. Carcinog., 10:35), and a linkage of environmental estrogens to increased risk of breast and other cancers (Colditz, G. A. (1998) J. Natl. Cancer Inst., 90:814-823). These effects are thought to be mediated predominantly by ERs.

ERs function as ligand-activated transcription factors and known ER targets include genes, such as c-myc, PR, cyclin D1, and TGFα, linked to promotion of cell proliferation and other oncogenic traits such as cell motility and invasion (Petz et al. (2000) Mol. Endocrinol., 14:972-985: Sabbah et al. (1999) Proc. Natl. Acad. Sci., 96:11217-11222; Vyhlidal et al. (2000) J. Mol. Endocrinol., 24:329-338). Similar to other transcriptional activators, the ER-dependent gene transcription requires interaction of ERs with transcriptional co-regulators, such as steroid receptor coactivators (SRCs; Johnson et al. (2011) Nat. Med., 17:660-661; Johnson et al. (2012) Mol. Cell Endocrinol., 348:430-439; Xu et al. (2003) Mol. Endocrinol., 17:1681-1692; Xu et al. (2009) Nat. Rev. Cancer 9:615-630) and co-integrators, such as p300/CBP (Chakravarti et al. (1996) Nature 383:99-103; Kamei et al. (1996) Cell 85:403-414). The importance of transcriptional co-regulators is emphasized by the requirement of SRC-3 in development and estrogenic response of the mammary gland in mice (Xu et al. (2000) Proc. Natl. Acad. Sci., 97:6379-6384; Wang et al. (2000) Proc. Natl. Acad. Sci., 97:13549-13554) and by studies demonstrating that overexpression of SRC-3 in human breast cancer cell lines and patient tumors is associated with resistance to anti-estrogen therapy (Osborne et al. (2003) J. Natl. Cancer Inst., 95:353-361). There is a strong need to understand the role of other effectors of ERs in breast cancer for diagnostic and therapeutic methods.

SUMMARY OF THE INVENTION

In accordance with one aspect of the instant invention, methods for treating cancer, particularly breast cancer, in a subject are provided. In a particular embodiment, the method comprises determining the cellular localization/overexpression of alteration/deficiency in activation-3 (ADA3) in a biological sample obtained from the subject and administering hormonal therapy (e.g., the administration of at least one estrogen receptor modulator or aromatase inhibitor) to the subject when ADA3 is determined to be predominantly nuclear and administering human epidermal growth factor receptor 2 (HER2) targeted therapy (e.g., the administration of at least one inhibitor of HER2 or antibody immunologically specific for HER2) and/or cyclin dependent kinase 2 (CDK2) targeted therapy (e.g., the administration of at least one CDK2 inhibitor (e.g., SNS-032, dinaciclib, etc.) when ADA3 is determined to be predominantly cytoplasmic or is overexpressed. The methods may further comprise detecting at least one other breast cancer marker in the biological sample. For example, the method may further comprise detecting (e.g., the presence and/or amount) of estrogen receptor (ER), progesterone receptor (PR). HER2, and/or epidermal growth factor receptor (EGFR). The subject may be administered hormonal therapy when ADA3 is determined to be predominantly nuclear and the biological sample is positive for ER and/or PR. The subject may be administered HER2-targeted therapy when ADA3 is determined to be predominantly cytoplasmic or overexpressed and the biological sample is positive for HER2 and/or EGFR. The methods may further comprise the administration of at least one other chemotherapeutic agent, treating the subject with radiation, and/or resecting cancerous cells/tissue from the subject. In a particular embodiment, the biological sample is a breast tissue sample or a tumor biopsy.

In accordance with another aspect of the instant invention, methods of providing a prognosis for cancer, particularly breast cancer, in a subject are provided. In a particular embodiment, the method comprises determining the cellular localization/overexpression of ADA3 in a biological sample obtained from the subject; wherein predominant nuclear localization of ADA3 is indicative of a good or excellent prognosis and predominant cytoplasmic localization/overexpression of ADA3 is indicative of a poor prognosis. The method may further comprise detecting at least one other breast cancer marker in the biological sample. For example, the method may further comprise detecting (e.g., the presence and/or amount) of ER, PR, HER2, and/or EGFR. The predominant nuclear localization of ADA3 and the presence of ER and/or PR in the biological sample are indicative of a good or excellent prognosis. The predominant cytoplasmic localization/overexpression of ADA3 and the presence of HER2 and/or EGFR in the biological sample are indicative of a poor prognosis.

In accordance with another aspect of the instant invention, kits are provided. The kits may be used for the diagnosis and/or prognosis of cancer, particularly breast cancer in a subject. In a particular embodiment, the kit comprises a first composition comprising at least one ADA3 antibody and at least one second composition comprising at least one agent for detecting another breast cancer marker. For example, the kit may comprise compositions containing agents for detecting ER, PR, HER2, and/or EGFR. In a particular embodiment, the agent is an antibody immunologically specific for the breast cancer marker.

In accordance with yet another aspect of the instant invention, methods for screening for therapeutic agents to treat cancer, particularly breast cancer, are provided. In a particular embodiment, the method comprises contacting cells having cytoplasmic ADA3 or overexpression with at least one agent and determining the ADA3 localization or overexpression within the treated cells, wherein a reduction in the amount of ADA3 in the cytoplasm, an increase in the amount of ADA3 in the nucleus (e.g., movement of ADA3 to the nucleus), and/or a decrease in the amount of ADA3 in the cell indicates the agent is a therapeutic agent for treating breast cancer.

BRIEF DESCRIPTION OF THE DRAWINGS

FIGS. 1A-1D show the characterization of ADA3 monoclonal antibody specificity for IHC staining.

FIGS. 2A and 2D: ×20; FIGS. 2B, 2C, and 2E: ×40.

FIGS. 3A and 3B provide Kaplan-Meier plots of nuclear (FIG. 3A) or cytoplasmic (FIG. 3B) ADA3 expression in the whole series of breast cancer patients with respect to breast cancer specific survival (BCSS) for 250 months. Kaplan-Meier plots of association of ADA3 nuclear (FIGS. 3C, 3D), and ADA3 cytoplasmic (FIGS. 3E, 3F) expression and ER expression in the whole series of breast cancer patients are also provided with respect to BCSS and distant metastasis free survival (DMFS) for 250 months. Kaplan-Meier plot of breast cancer patients with cytoplasmic ADA3 and HER2/ErbB2 (FIG. 3G) or epidermal growth factor receptor (EGFR) (FIG. 3H) are also provided with respect to BCSS (FIGS. 3G, 3H) and DMFS (FIGS. 3I, 3J) for 250 months.

DETAILED DESCRIPTION OF THE INVENTION

The novel ER coactivator alteration/deficiency in activation-3 (ADA3) is an essential adaptor component of ADA histone acetyltransferase (HAT) complex initially identified in yeast where it bridges transcription factor interacting component ADA2 with HAT enzymatic component GCN5. Mammals possess several distinct ADA3-containing HAT complexes with different subunit composition and multiple HAT enzymatic components including GCN5, PCAF, and p300/CBP (Lee et al. (2007) Nat. Rev. Mol. Cell Biol., 8:284-295). Human ADA3 directly interacts with ERα, and chromatin immunoprecipitation analyses demonstrated that ADA3 is a component of ER-associated HAT complexes bound to native promoter of the estrogen-responsive gene pS2 (Meng et al. (2004) J. Biol. Chem., 279:54230-54240; Germaniuk-Kurowska et al. (2007) Cancer Res., 67:11789-11797). Using RNAi knockdown, endogenous ADA3 was shown to be required for estrogen-induced increase in the expression of widely studied ER-responsive target genes such as pS2, cathepsin D, and PR (Meng et al. (2004) J. Biol. Chem., 279:54230-54240; Germaniuk-Kurowska et al. (2007) Cancer Res., 67:11789-11797).

Herein, the significance of ADA3 overexpression/localization in human breast cancer patients was assessed. Tissue microarrays prepared from large series of breast cancer patients with long-term follow-ups were stained with anti-ADA3 monoclonal antibody using immunohistochemistry. Samples were analyzed for ADA3 expression followed by correlation with various clinicopathological parameters and patients' outcomes. It was determined that breast cancer specimens show predominant nuclear, cytoplasmic, or mixed nuclear and cytoplasmicADA3 staining patterns. Predominant nuclear ADA3 staining correlated with ER+ status. While predominant cytoplasmic ADA3 staining negatively correlated with ER+ status, but positively correlated with ErbB2, EGFR, and Ki67. Furthermore, a positive correlation of cytoplasmic/overexpression of ADA3 was observed with higher histological grade, mitotic counts, Nottingham Prognostic Index, and positive vascular invasion. Patients with nuclear ADA3 and ER positivity have better breast cancer specific survival and distant metastasis free survival. Significantly, cytoplasmic/overexpression of ADA3 showed a strong positive association with reduced BCSS and DMFS in ErbB2+/EGFR+ patients. Although in multivariate analyses ADA3 expression was not an independent marker of survival, predominant nuclear ADA3 staining in breast cancer tissues correlates with ER+ expression and together serves as a marker of good prognosis, whereas predominant cytoplasmic ADA3 expression correlates with ErbB2+/EGFR+ expression and together is a marker of poor prognosis. Thus, ADA3 cytoplasmic localization/overexpression together with ErbB2+/EGFR+ status serves as better prognostic marker than individual proteins to predict survival of patients. These results indicate the prognostic value of ADA3 expression in breast cancer.

In accordance with the instant invention, methods of identifying, determining an increased risk for, diagnosing, and/or prognosis of a cancer, particularly breast cancer, in a patient are provided. In a particular embodiment, the method comprises determining the localization/overexpression of ADA3 (e.g., GenBank Gene ID: 10474). More particularly, the method may comprise determining the cellular location/overexpression of ADA3 (e.g., nuclear and/or cytoplasmic). The methods may further comprise obtaining a biological sample from the subject. In a particular embodiment, the biological sample is tumor tissue or breast tissue. The method may further comprise detecting the presence of at least one other cancer marker (e.g., a breast cancer marker). For example, the methods may further comprise detecting the presence and/or amount of ER, PR, HER2/ErbB2, vascular endothelial growth factor (VEGF) or vascular endothelial growth factor receptor (VEGFR), and/or EGFR.

As explained hereinbelow, when ADA3 is predominantly (e.g., >50%) found in the nucleus, the subject has a good or excellent prognosis (e.g., by the Nottingham Prognostic Index). When ADA3 is predominantly (e.g., >50%) found in the cytoplasm, the subject has a poor prognosis (e.g., by the Nottingham Prognostic Index) with increased risk of metastasis and higher risk of death. The Nottingham Prognostic Index is well known in the art (see, e.g., Haybittle et al. (1982) Br. J. Cancer 45:361-6; Yu et al. (2004) Cancer Res., 64:2962-8; Elston et al. (1991) Histopathology 19:403-410; Galea et al. (1992) Breast Cancer Res. Treat., 22:207-219; Ellis et al. (1992) Histopathology 479-489; Balslev et al. (1994) Breast Cancer Res. Treat., 32:281-290; Sauerbrei et al. (1997) Breast Cancer Res. Treat., 42:149-163). As used herein, a subject with a score of 3.4 or less is categorized as in the excellent prognostic group, a patient with a score of between 3.4 and 5.4 is categorized to as in a good (moderate) prognostic group, and a patient with a score of greater than 5.4 is categorized as in a poor prognostic group. Moreover, when ADA3 is predominantly found in the nucleus and the sample is ER and/or PR positive, the subject has a good or excellent prognosis. However, when ADA3 is predominantly found in the cytoplasm and the sample is HER2/ErbB2 and/or EGFR positive, the subject has a poor prognosis.

The ability to detect the above markers—either as a nucleic acid molecule or as a protein—is well known in the art. In a particular embodiment, the markers, particularly ADA3, are detected as proteins. For example, the markers may be detected with antibodies which are immunologically specific for the marker (e.g., via immunohistochemistry). Anti-ADA3 antibodies of the instant invention include, without limitation, monoclonal antibodies, polyclonal antibodies, and fragments thereof. The anti-ADA3 antibodies may also be immunologically specific for modified forms of ADA3 such as phosphorylated ADA3, ubiquitinated ADA3, sumoylated ADA3, or acetylated ADA3. ADA3 is phosphorylated by cyclin dependent kinase 2 (CDK2), a known regulator of cell cycle. Thus, breast cancers with cytoplasmic ADA3 or overexpressed ADA3 may be treated with conventional treatment regimen combined with CDK2 inhibitors. Further, in accordance with the instant invention, ADA3 localization/expression serves as a marker for the effectiveness of this treatment.

The methods may further comprise treating the diagnosed patient. In general, a patient with a good or excellent prognosis may be treated with a conventional treatment regimen. A patient with a poor prognosis may be treated with an alternative or more aggressive regimen. In other words, upon diagnosing the patient by the methods of the instant invention, the poor prognosis patient will not have to wait for the conventional treatment regimen to fail before moving onto the more aggressive treatment. Furthermore, knowledge of the likely clinical course of the disease allows the patient to have a more realistic expectation of the outcome of the cancer treatment.

When ADA3 is predominantly nuclear, the breast cancer may be treated by administration of hormonal therapy, particularly anti-estrogen therapy, to the subject. As used herein, "hormonal therapy" refers to drugs or treatments that block the effect of, or reduce the levels of hormones, particularly those which block the effect of estrogen including anti-estrogen therapy and estrogen ablation therapy. Examples include, without limitation, antagonists of the estrogen receptor or selective estrogen receptor modulators (e.g., tamoxifen, toremifene, lasofoxifene, raloxifene, afimoxifene, arzoxifene, bazedoxifene, ormeloxifene, fulvestrant) and aromatase inhibitors (steroidal or nonsteroidal; e.g., letrozole, anastrozole, aminoglutethimide, fadrozole, vorozole, exemestane, formestane, testolactone). When ADA3 is predominantly cytoplasmic or is overexpressed, the breast cancer may be treated with HER2/ErbB2 targeted therapy. Examples include, without limitation: inhibitors of HER2 (e.g., lapatinib, neratinib, afatinib) and antibodies immunologically specific for HER2 (e.g., trastuzumab, pertuzumab). In a particular embodiment, a combination of HER2/ErbB2 targeted therapies are administered (e.g., a combination of anti-HER2 antibodies (e.g., at least two antibodies which recognize different/distinct epitopes of HER2 or at least one anti-HER2 antibody and at least one HER2 inhibitor). The methods of the instant invention may also comprise the administration of at least one other chemotherapeutic agent or anti cancer therapy (e.g., radiation and/or surgery to remove cancerous cells or a tumor (e.g., resection)). The agents administered to the subject may be contained with a composition comprising at least one pharmaceutically acceptable carrier. When more than one agent is being administered (e.g., trastuzumab with an additional chemotherapeutic agent), the agents may be administered separately (before or after) and/or at the same time. The agents may be administered in the same composition or in separate compositions.

In accordance with another aspect of the instant invention, methods of identifying an agent which is therapeutic for the treatment of breast cancer are provided. In a particular embodiment, the method comprises contacting cells comprising cytoplasmic ADA3 with at least one agent and determining the ADA3 localization, wherein a reduction in the amount of ADA3 in the cytoplasm and/or an increase in the amount of ADA3 in the nucleus indicates the agent is a therapeutic agent for treating breast cancer. The agents to be screened by the methods of the instant invention can be any compounds (e.g., isolated compounds), particularly any natural or synthetic chemical compounds (such as small molecule compounds), extracts (such as plant-, fungal-, prokaryotic- or animal-based extracts), organic compounds and molecules, inorganic compounds and molecules, biological macromolecules (such as saccharides, lipids, peptides, proteins, polypeptides and nucleic acid molecules (e.g., those encoding a protein of interest)), inhibitory nucleic acid molecule (e.g., antisense, shRNA, siRNA, miRNA etc.), and drugs (e.g., an FDA approved drug). In a particular embodiment, the agent is a small molecule.

In accordance with another aspect of the present invention, kits for identifying and/or diagnosing breast cancer are provided. In a particular embodiment, the kit comprises antibodies specific for ADA3. As stated hereinabove, the anti-ADA3 antibodies may be monoclonal or polyclonal, or fragments thereof. In a particular embodiment, the anti-ADA3 antibody is a monoclonal antibody. The anti-ADA3 antibodies may also be immunologically specific for modified forms of ADA3 such as phosphorylated ADA3, ubiquitinated ADA3, sumoylated ADA3, or acetylated ADA3. The antibodies of the kit may be lyophilized or maintained in a carrier. The kits may further comprise at least one other agent (e.g., nucleic acid probes, antibodies, etc.) for detecting the presence and/or amount of another cancer marker (e.g., ER, PR, HER2/ErbB2, VEGF or VEGFR and/or EGFR). In a particular embodiment, the kit comprises at least one other antibody immunologically specific for another cancer marker. The antibodies may be contained within the same composition or in separate compositions.

For example, the kit may comprise a first composition comprising at least one ADA3 antibody (optionally with at least one carrier) and a second composition comprising at least one other cancer marker antibody (optionally with at least one carrier). The kits may further comprise instruction material and/or at least one control (e.g., a sample, from a healthy subject, a sample with ADA3 nuclear localization and ER+, and/or a sample with ADA3 cytoplasmic localization or overexpression, HER2/ErbB2+, and EGFR+).

The compositions described herein will generally be administered to a subject or a patient as a pharmaceutical preparation. The term "patient" as used herein refers to human or animal subjects. These compositions may be employed therapeutically, under the guidance of a physician.

The compositions of the instant invention may be conveniently formulated for administration with any pharmaceutically acceptable carrier(s). For example, the agents may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The dose and dosage regimen of compositions according to the invention that are suitable for administration to a particular patient may be determined by a physician considering the patient's age, sex, weight, general medical condition, and the specific condition for which the composition is being administered and the severity thereof. The physician may also take into account the route of administration, the pharmaceutical carrier, and the composition's biological activity.

Selection of a suitable pharmaceutical preparation will also depend upon the mode of administration chosen. For example, the compositions of the invention may be administered intravenously. In this instance, a pharmaceutical preparation comprises the agents dispersed in a medium that is compatible with intravenous injection.

Compositions of the instant invention may be administered by any method. For example, the compositions of the instant invention can be administered, without limitation, parenterally, subcutaneously, orally (e.g., liquid or pill/capsule/tablet form), topically, pulmonarily, intravenously, intraperitoneally, intrathecally, epidurally, intramuscularly, intradermally. Pharmaceutical preparations for injection and oral administration are known in the art. If injection is selected as a method for administering the composition, steps must be taken to ensure that sufficient amounts of the molecules reach their target cells to exert a biological effect.

Pharmaceutical compositions containing an agent of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of compositions of the instant invention may be determined by evaluating the toxicity of the molecules or cells in animal models. Various concentrations of agents in pharmaceutical preparations may be administered to mice, and the minimal and maximal dosages may be determined based on the beneficial results and side effects observed as a result of the treatment. Appropriate dosage unit may also be determined by assessing the efficacy of the agent treatment in combination with other standard drugs. The dosage units of the compositions may be determined individually or in combination with each treatment according to the effect detected.

The pharmaceutical preparation comprising the agents of the instant invention may be administered at appropriate intervals, for example, at least once or twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

As used herein, a "biological sample" refers to a sample of biological material obtained from a subject, preferably a human subject, including a tissue, a tissue sample, a cell sample, a tumor sample, and a biological fluid, e.g., blood or urine. A biological sample may be obtained in the form of, e.g., a tissue biopsy, such as, an aspiration biopsy, a brush biopsy, a surface biopsy, a needle biopsy, a punch biopsy, an excision biopsy, an open biopsy, an incision biopsy and an endoscopic biopsy.

As used herein, "diagnose" refers to detecting and identifying a disease in a subject. The term may also encompass assessing or evaluating the disease status (progression, regression, stabilization, response to treatment, etc.) in a patient known to have the disease.

As used herein, the term "prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis). In other words, the term "prognosis" refers to providing a prediction of the probable course and outcome of a cancer or the likelihood of recovery from the cancer. The term "prognosis" is recognized in the art and encompasses predictions about the likely course of disease or disease progression, particularly with respect to likelihood of disease remission, disease relapse, tumor recurrence, metastasis, and death. A "good prognosis" may refer to the likelihood that a patient afflicted with cancer will remain cancer-free after therapy. A "poor prognosis" may refer to the likelihood of a relapse or recurrence of the underlying cancer or tumor after treatment, the likelihood of developing metastases, and/or the likelihood of death. In particular embodiments, the time frame for assessing prognosis is, for example, less than one year, one, two, three, four, five, six, seven, eight, nine, ten, fifteen, twenty, or more years.

The term "treat" as used herein refers to any type of treatment that imparts a benefit to a patient afflicted with a disease, including improvement in the condition of the patient (e.g., in one or more symptoms), delay in the progression of the condition, etc.

The phrase "effective amount" refers to that amount of therapeutic agent that results in an improvement in the patient's condition.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween® 80, Polysorbate 80), emulsifier, buffer (e.g., Tris HCl, acetate, phosphate), water, aqueous solutions, oils, bulking substance (e.g., lactose, mannitol), excipient, auxillary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.). American Pharmaceutical Association, Washington.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 10-100, about 10-50, about 15-30, about 15-25, about 20-50, or more nucleotides, although it may contain fewer nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and molecules comprising immunologically active portions/fragments of an immunoglobulin molecule such as, without limitation: Fab, Fab', F(ab')$_2$, F(v), scFv, scFv$_2$, scFv-Fc, minibody, diabody, tetrabody, and single variable domain (e.g., variable heavy domain, variable light domain).

With respect to antibodies, the term "immunologically specific" refers to antibodies that bind to one or more epitopes of a protein or compound of interest, but which do not substantially recognize and bind other molecules in a sample containing a mixed population of antigenic biological molecules.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

As used herein, an "instructional material" includes a publication, a recording, a diagram, or any other medium of expression which can be used to communicate the usefulness of the composition of the invention for performing a method of the invention.

As used herein, the term "small molecule" refers to a substance or compound that has a relatively low molecular weight (e.g., less than 2,000). Typically, small molecules are organic, but are not proteins, polypeptides, or nucleic acids.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, and Pseudomonas exotoxin); taxanes; alkylating agents (e.g., temozolomide, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); anthracyclines; and tubulin interactive agents (e.g., vincristine, vinblastine, and paclitaxel (Taxol®)).

Radiation therapy refers to the use of high-energy radiation from x-rays, gamma rays, neutrons, protons and other sources to target cancer cells. Radiation may be administered externally or it may be administered using radioactive material given internally. Chemoradiation therapy combines chemotherapy and radiation therapy.

The following example is provided to illustrate certain embodiments of the invention. It is not intended to limit the invention in any way.

Example

Materials and Methods
Patient Population and Tissue Microarrays

Tissue microarrays (TMAs) were prepared from formalin-fixed, paraffin-embedded tissue specimens that include a series of primary operable (stage I and II) breast carcinoma cases of age<70 presented consecutively between 1988 and 1998 at the Nottingham Breast Unit with tumors of less than 5 cm diameter (Abd El-Rehim et al. (2005) Int. J. Cancer 116:340-350). This is a well-characterized series (900 cases) that includes clinical and pathological data (Elston et al. (1991) Histopathology 19:403-410). The breast cancer specific survival (BCSS) is defined as time (in months) from the date of primary surgery to the date of breast cancer-related death. Distant metastasis free survival (DMFS) is defined as duration (in months) from the date of primary surgery to the appearance of distant metastasis. The median age of patients was 55 years (range 18-70 years) with a median BCSS of 129 months (range 4-243 months) and median time of DMFS of 114 months (range 5-241 months). Distant recurrence occurred in 249 cases (31%); 228 (29%) patients died from breast cancer, while 435 (56%) patients were alive at the end of follow-up. Adjuvant systemic therapies were provided according to the Nottingham Prognostic Index (NPI) group. Systemic therapy was prescribed to the Excellent (NPI≤3.4) and Good (NPI 3.41-5.4) prognostic Groups. The Moderate I group received hormonal therapy for ER+ tumors. The Moderate II, Poor, and Very Poor Groups received hormone therapy for ER+ tumors and cytotoxic therapy for ER−. Of the informative cases (n=801) 360 have received hormone therapy (45%) while 201 cases received chemotherapy (25%). None of the patients received neo-adjuvant therapy or anti-HER2 targeted therapy.

Validation of ADA3 Antibody Specificity in IHC

An anti-ADA3 monoclonal antibody has been generated that specifically recognizes human and mouse ADA3 in western blotting and immunoprecipitation (Mohibi et al. (2012) J. Biol. Chem., 287:29442-56). To validate the specificity of monoclonal anti-ADA3 antibody 5C9/C8 in IHC analyses, 76N-TERT cells (hTERT-immortalized normal human mammary epithelial cells-hMECs) or a retroviral transductant overexpressing FLAG-hADA3 as well as mouse embryonic fibroblasts (MEFs) derived from Ada3$^{-/-}$ mice (Mohibi et al. (2012) J. Biol. Chem., 287:29442-56) infected with a control adenovirus or adenoviral Cre (Ada3$^{-/-}$ MEFs) were cultured on coverslips, fixed with 4% paraformaldehyde, and immunostained with anti-ADA3 antibody, using the procedure as described (Zhao et al. (2012) Breast Cancer Res. Treat., 134:171-80). Western blotting was performed on whole cell lysates with a 1:4,000 dilution of anti-ADA3 antibody (Mohibi et al. (2012) J. Biol. Chem., 287:29442-56). Breast cancer TMAs were immunostained as described (Zhao et al. (2012) Breast Cancer Res. Treat., 134:171-80). Briefly, breast cancer TMAs (Mc-Carty et al. (1985) Arch. Pathol. Lab Med., 109:716-721) were deparaffinized in xylene, rehydrated in descending alcohols, and treated in a digital pressure cooker containing citrate buffer (pH 6.0: DakoCytomation S 1699). Endogenous peroxidase activity was blocked by incubation in 3% hydrogen peroxide for 10 minutes. The sections were rinsed in TBST and incubated for 15 minutes in Protein-Block buffer (DakoCytomation X0909); the sections were then incubated overnight at 4° C. with (1:2000) dilution of anti-ADA3 monoclonal antibody (5C9/C8).

Scoring of TMA Cores

Of the 900 breast cancer samples analyzed as TMAs, sufficient tissue was available to perform scoring in 803 cases and these form the basis of analyses presented in this study. Normal controls included 25 normal human breast tissue specimens. Semi-quantitative assessment of staining intensity utilized a modified histochemical score (H-score) that includes the intensity of staining and the percentage of stained cells. The intensity of staining was scored on a scale of 0 to 3 corresponding to negative (0), weak (1), moderate (2), and strong (3) staining. Percentage of positive cells was visually estimated. Multiplication of the two indices (intensity and percentage positive cells) provided final scores that range from 0 to 300. The pattern of expression was visually recorded as nuclear, cytoplasmic, or combined nuclear and cytoplasmic or no nuclear/cytoplasmic staining. Any nuclear expression (>1%; 41% cases) was considered positive, while cytoplasmic expression was considered positive if it exceeded a cut-off of an H-score of 110, which is based on histogram distribution of the cases as well as X-Tile computer software analysis (Camp et al. (2004) Clin. Cancer Res., 10:7252-7259) (Table 1). All cases were scored without prior knowledge of the clinicopathological parameters or outcome data. In tables and figures cytoplasmic positive include cytoplasmic positive cases despite of nuclear-negativity or positivity; similarly nuclear positive cases include nuclear positive regardless of cytoplasmic staining status.

TABLE 1

Nuclear and cytoplasmic expression of ADA3 in breast cancer tissue specimens.

| ADA3 nuclear expression | ADA3 cytoplamic expression | | |
|---|---|---|---|
| | Negative | Positive | Total |
| Nagative | 50 (6.3%) | 427 (53.3%) | 477 (59.6%) |
| Positive | 103 (12.9%) | 221 (27.5%) | 324 (40.4%) |
| Total | 153 (19.2%) | 648 (80.8%) | 801 |

Statistical Analysis

Statistical analysis was performed using the SPSS 16.0 statistical software (SPSS Inc., Chicago, Ill., USA). The cut-off values for various biomarkers included in this study were the same as previously published for this patient series (Rakha et al. (2007) J. Clin. Oncol., 25:4772-4778; Rakha et al. (2006) J. Pathol., 208:495-506). Optimal cut-offs for ADA3 expression were determined using the X-tile bioinformatics software (version 3.6.1, 2003-2005, Yale University, USA). Analysis of categorical variables was performed with $\chi^2$ test. Survival curves were analyzed using the Kaplan-Meier method with significance determined by the Log Rank test. Multivariate analysis was performed using the Cox hazard analysis. A p value (two-sided) of <0.05 was considered significant.

Results
Validation of the Specificity of Anti-ADA3 Monoclonal Antibody for IHC

Figure 1:
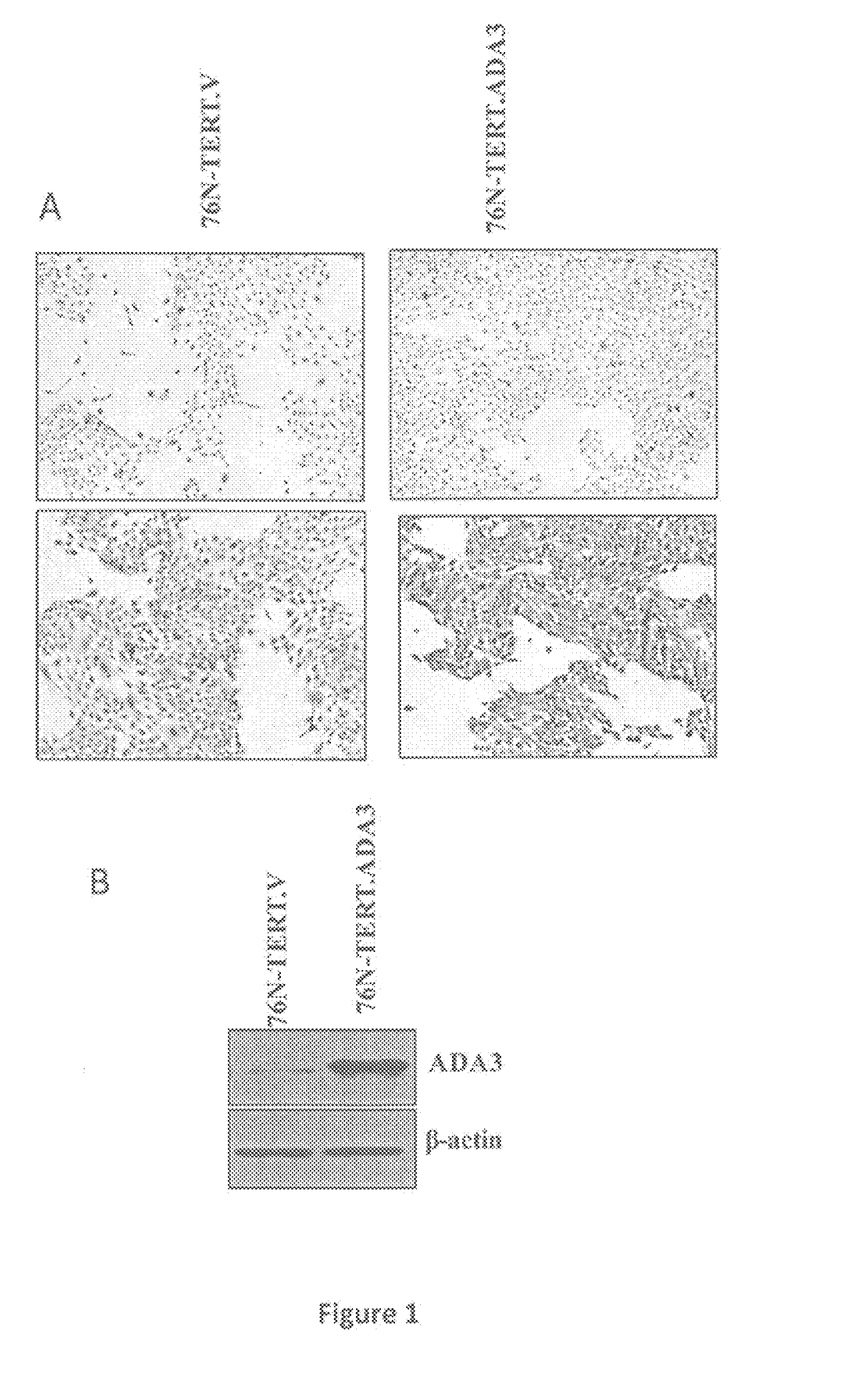
FIG. 1A shows IHC staining of vector and FLAG-tagged ADA3 overexpressing immortalized normal mammary epithelial cells (76N-TERT), using ADA3 mAb and mouse IgG (control).
FIG. 1B shows Western blotting of 76N-TERT cells transfected with vector or hADA3.
FIG. 1C shows IHC staining of ADA3$^{fl/fl}$ and knock out MEFs.
FIG. 1D shows Western blotting of ADA3$^{fl/fl}$ and ADA3$^{-/-}$ MEFs.

In order to assess the robustness and specificity of this antibody. IHC analysis was performed on 76N-TERT cell line that overexpresses FLAG-hADA3. As expected, essentially no staining was observed with the IgG negative control, whereas vector-infected cells showed majority nuclear and weak cytoplasmic ADA3 staining as compared to ADA3-overexpressing cell line in which, both strong nuclear and strong cytoplasmic signal was observed (FIG. 1A). Western blotting showed high ADA3 expression that correlated with IHC staining (FIG. 1B). Next, Ada3-null mouse embryonic fibroblasts (MEFs) by adenovirus-Cre infection of Ada3$^{fl/fl}$ MEFs were used (Mohibi et al. (2012) J. Biol. Chem., 287:29442-56). While specific ADA3 staining was seen in parental Ada3$^{fl/fl}$ MEFs, no staining was seen in MEFs with Cre-induced Ada3 deletion (FIGS. 1C, 1D). Altogether, these initial studies validated the use of mAb 5C9/C8 for IHC-based detection of ADA3.

Figure 2:
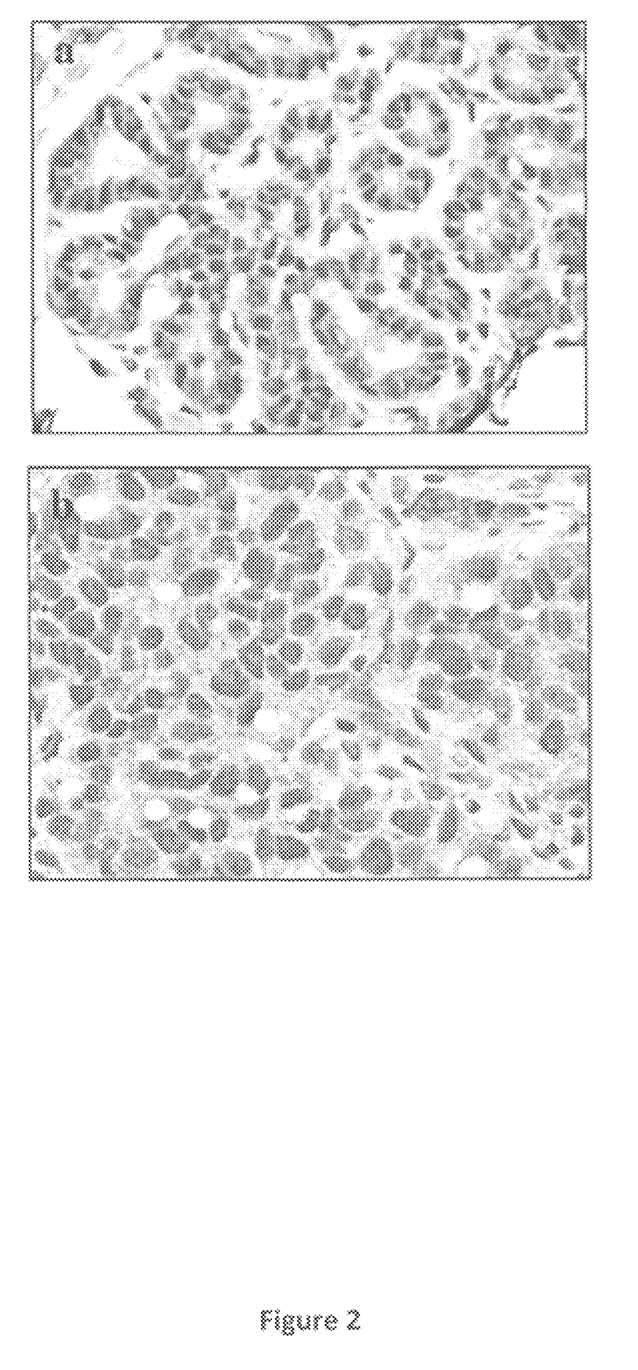
FIGS. 2A-2E show ADA3 expression in representative normal and breast cancer tissue sections. ADA3 staining of normal breast tissue shows a basal level of nuclear ADA3 expression (FIG. 2A). Breast cancer specimens showing only predominantly nuclear (FIG. 2B), predominantly cytoplasmic (FIG. 2C) strong nuclear and cytoplasmic (FIG. 2D) and no staining of ADA3 (FIG. 2E) are also provided. Magnification.

ADA3 Protein is Localized to Both Nucleus and Cytoplasm in Breast Cancer Tissue Specimens Next, IHC analysis of ADA3 expression in TMAs was performed. In normal breast tissue specimens, heterogeneous ADA3 expression was observed in both epithelial and myoepithelial cells lining the ducts (FIG. 2A). Across the panel of breast cancer specimens, ADA3 in tumor cells was variable in degree and site of expression (FIGS. 2B, 2C, 2D, 2E). In tumor tissues four patterns of ADA3 staining were observed as either strong nuclear as in normal ducts (FIG. 2B), strong cytoplasmic (FIG. 2C), strong nuclear and cytoplasmic (FIG. 2D) or barely detectable staining (FIG. 2E). Therefore, ADA3 expression was assessed as strong cytoplasmic (cytoplasmic+), strong nuclear (nuclear+), or completely absent in malignant cells (Table 1). Overall, predominant nuclear, cytoplasmic, and mixed (cytoplasmic+ nuclear) ADA3 staining was seen in 13, 53, and 28% of the 801 breast cancer specimens analyzed, respectively. Notably, about 6% of specimens showed a complete absence of ADA3 expression (Table 1).

Correlation of ADA3 Expression with Clinicopathological Parameters

Next, the association of nuclear and cytoplasmic ADA3 expression with clinicopathological variables was assessed (Table 2). Nuclear ADA3 expression was associated with more differentiated tumors (grade 1 and 2), lower degree of cellular pleomorphism (p≤0.001), low proliferation status, the absence of vascular invasion (p=0.008), and excellent to good NPI. On the other hand, cytoplasmic ADA3 expression was associated with morphological and molecular features of aggressive behavior in cancer including a higher histological grade (grade 3), a high degree of cellular pleomorphism/nuclear atypia (p≤0.001), and high proliferation status, positive vascular invasion, and poorer NPI (Table 2). Regarding ADA3 expression and tumor subtypes, invasive lobular carcinoma, which are usually ER-positive (>90% ER+), showed more frequent nuclear expression and less cytoplasmic positivity compared to invasive ductal carcinomas/no special type (Table 3).

TABLE 2

Relationship between ADA3 expression and clinicopathological parameters.

| | ADA3 nuclear expression | | | ADA3 cytoplasmic expression | | |
|---|---|---|---|---|---|---|
| Variables | Negative N (%) | Positive N (%) | p value | Negative N (%) | Positive N (%) | p value |
| Patient age | | | | | | |
| Mean (range) years | 55 (28-69) | 54 (18-70) | 0.500 | 56 (28-70) | 54 (18-70) | 0.133 |
| Menopausal status | | | | | | |
| Premenopausal | 180 (38.1) | 108 (33.8) | | 43 (28.5) | 247 (38.4) | |
| Postmenopausal | 293 (61.9) | 212 (66.2) | 0.216 | 108 (71.5) | 397 (61.6) | 0.023 |
| Tumor size (cm) | | | | | | |
| ≤1.5 | 98 (20.7) | 92 (28.3) | | 36 (23.8) | 155 (24) | |
| >1.5 | 375 (79.3) | 233 (71.7) | 0.013 | 115 (76.2) | 490 (76) | 0.961 |
| Lymph node stage | | | | | | |
| 1 | 261 (55.2) | 195 (60) | | 97 (64.2) | 358 (55.5) | |
| 2 | 160 (33.8) | 104 (32) | | 38 (25.2) | 225 (34.9) | |
| 3 | 52 (11) | 26 (8) | 0.254 | 16 (10.6) | 62 (9.6) | 0.072 |
| Tumor grade | | | | | | |
| 1 | 51 (10.8) | 68 (20.9) | | 24 (15.9) | 95 (14.7) | |
| 2 | 136 (28.8) | 134 (41.2) | | 72 (47.7) | 198 (30.7) | |
| 3 | 286 (60.5) | 123 (37.8) | <0.001 | 55 (36.4) | 352 (54.6) | <0.001 |
| Mitotic counts | | | | | | |
| 1 | 121 (26.3) | 138 (44.4) | | 78 (54.2) | 182 (29) | |
| 2 | 81 (17.6) | 64 (20.6) | | 19 (13.2) | 126 (20.1) | |
| 3 | 258 (56.1) | 109 (35) | <0.001 | 47 (32.6) | 319 (50.9) | 0.001 |
| NPI | | | | | | |
| Poor | 107 (22.6) | 118 (36.3) | | 16 (10.6) | 128 (19.8) | |
| Moderate | 266 (56.2) | 170 (52.3) | | 78 (51.7) | 356 (55.2) | |
| Good | 100 (21.1) | 118 (36.3) | <0.001 | 57 (37.7) | 161 (25) | 0.001 |
| Distance Metastasis | | | | | | |
| No | 313 (66.7) | 228 (70.8) | | 112 (74.7) | 428 (67) | |
| Positive | 156 (33.3) | 94 (29.2) | 0.226 | 38 (25.3) | 211 (33) | 0.068 |
| Regional recurrence | | | | | | |
| No | 412 (89.2) | 281 (88.9) | | 130 (88.4) | 561 (89.2) | |
| Positive | 50 (10.8) | 35 (11.1) | 0.911 | 17 (11.6) | 68 (10.8) | 0.792 |

TABLE 2-continued

Relationship between ADA3 expression and clinicopathological parameters.

|  | ADA3 nuclear expression | | | ADA3 cytoplasmic expression | | |
|---|---|---|---|---|---|---|
| Variables | Negative N (%) | Positive N (%) | p value | Negative N (%) | Positive N (%) | p value |
| Vascular invasion | | | | | | |
| No | 241 (56.3) | 183 (66.3) | | 99 (75.6) | 324 (56.7) | |
| Positive | 187 (43.7) | 93 (33.7) | 0.008 | 32 (24.4) | 247 (43.3) | <0.001 |

TABLE 3

Correlations of ADA3 expression with breast cancer histological subtypes.

| Tumor type | Negative N (%) | Positive N (%) | p value |
|---|---|---|---|
| ADA3 cytoplasmic expression | | | |
| Invasive ductal/no special type (NST) | 60 (41) | 411 (65) | |
| Invasive lobular | 46 (31) | 41 (7) | |
| Mixed NST and lobular | 10 (7) | 19 (3) | |
| Mixed NST and a special type | 2 (1) | 14 (2) | |
| Tubular mixed | 22 (15) | 114 (18) | |
| Tubular | 2 (1) | 18 (3) | |
| Mucinous | 0 (0) | 4 (1) | |
| Total | 148 | 629 | <0.001 |
| ADA3 nuclear expression | | | |
| Invasive ductal/no special type (NST) | 321 (70) | 152 (48) | |
| Invasive lobular | 33 (7) | 53 (17) | |
| Mixed NST and lobular | 13 (3) | 16 (5) | |
| Mixed NST and special type | 18 (4) | 12 (4) | |
| Tubular mixed | 65 (14) | 71 (23) | |
| Tubular | 10 (2) | 10 (3) | |
| Mucinous | 2 (1) | 2 (1) | |
| Total | 462 | 316 | <0.001 |

Association of ADA3 Expression with Established Breast Cancer Biomarkers

Next, ADA3 localization was correlated with known biomarkers (Table 4). Predominant nuclear ADA3 staining showed a strong positive association with ER and PR positive status (p<0.001, <0.001); positive staining for BRCA1 (p<0.001), a known tumor suppressor in breast cancer (Rosen et al. (2005) Endocr. Relat. Cancer 12:533-548; Miki et al. (1994) Science 266:66-71); and with positive staining for cytokeratin 18 (p=0.004), a luminal marker. However, no correlation with cytokeratin 19 (p=0.08), a marker of more differentiated luminal cells was observed (Table 4). These results indicate a positive association between nuclear ADA3 staining and positive staining for markers of ER+ luminal breast cancers.

Notably, predominant cytoplasmic ADA3 staining showed a negative association with ER (p<0.001) and PR (p=0.005) but a positive association with HER2 (p=0.024) and EGFR (p=0.011) positivity. Consistently, predominant cytoplasmic ADA3 staining showed a positive association with increased tumor growth fraction, previously assessed on full face tissue sections using MIB1 labeling index (p<0.001), p53 (p=0.001), and basal cytokeratin CK17 (p=0.007). However, no association was observed between cytoplasmic ADA3 staining and CK5/6, CK14, and p63 positivity (myoepithelial/basal markers) (Table 4). These results indicate a strong correlation of predominant cytoplasmic ADA3 staining with ErbB2 and EGFR expressing breast cancers.

TABLE 4

Relationship between ADA3 expression and other biomarkers.

| Variables | Negative N (%) | Positive N (%) | p value |
|---|---|---|---|
| | ADA3 nuclear expression | | |
| Hormone receptor ER | | | |
| Negative | 157 (34.3) | 49 (15.7) | |
| Positive | 301 (65.7) | 263 (84.3) | <0.001 |
| PgR | | | |
| Negative | 218 (48.7) | 230 (51.3) | |
| Positive | 102 (33) | 207 (67) | <0.001 |
| ER PgR | | | |
| ER + PR− | 65 (14.8) | 52 (17.3) | |
| ER − PR− | 147 (33.5) | 43 (14.3) | |
| ER + PR+ | 223 (50.8) | 202 (67.3) | |
| ER − PR+ | 4 (1) | 3 (1) | <0.001 |
| HER2 | | | |
| Negative | 386 (83.5) | 282 (88.4) | |
| Positive | 76 (16.5) | 37 (11.6) | 0.058 |
| Triple negative | | | |
| Non-TN | 352 (76.7) | 282 (90.1) | |
| TN | 107 (23.3) | 31 (9.9) | <0.001 |
| BRCA1 | | | |
| Negative | 221 (57.6) | 74 (28.1) | |
| Positive | 163 (42.4) | 189 (71.9) | <0.001 |
| MIB1 | | | |
| Negative | 102 (27.8) | 128 (47.9) | |
| Positive | 265 (72.2) | 139 (52.1) | <0.001 |
| EGFR | | | |
| Negative | 326 (79.5) | 237 (87.5) | |
| Positive | 84 (20.5) | 34 (12.5) | 0.007 |
| p63 | | | |
| Negative | 442 (98.7) | 313 (99.7) | |
| Positive | 6 (1.3) | 1 (0.3) | 0.146 |
| p53 | | | |
| Negative | 302 (67.7) | 241 (78) | |
| Positive | 144 (32.3) | 68 (22) | 0.002 |
| Cytokeratins CK 5/6 | | | |
| Negative | 378 (84) | 268 (87.9) | |
| Positive | 72 (16) | 37 (12.1) | 0.138 |
| CK 14 | | | |
| Negative | 407 (90.6) | 271 (89.1) | |
| Positive | 42 (9.4) | 31 (10.2) | 0.68 |
| CK 17 | | | |
| Negative | 332 (87.4) | 214 (87.7) | |
| Positive | 48 (12.6) | 30 (12.3) | 0.901 |

TABLE 4-continued

Relationship between ADA3 expression and other biomarkers.

| Variables | Negative N (%) | Positive N (%) | p value |
|---|---|---|---|
| CK 18 | | | |
| Negative | 73 (17) | 27 (9.5) | |
| Positive | 356 (83) | 258 (90.5) | 0.004 |
| CK 19 | | | |
| Negative | 49 (10.7) | 22 (7) | |
| Positive | 408 (89.3) | 292 (93) | 0.08 |
| ADA3 cytoplasmic expression | | | |
| Hormone receptor | | | |
| ER | | | |
| Negative | 20 (13.7) | 184 (29.6) | |
| Positive | 126 (86.3) | 438 (70.4) | <0.001 |
| PgR | | | |
| Negative | 45 (31.7) | 274 (44.6) | |
| Positive | 97 (68.3) | 340 (55.4) | 0.005 |
| ER PgR | | | |
| ER + PR− | 24 (17.3) | 93 (15.5) | |
| ER − PR− | 18 (12.9) | 171 (28.5) | |
| ER + PR+ | 95 (68.3) | 330 (55.1) | |
| ER − PR+ | 2 (1.4) | 5 (0.8%) | 0.002 |
| HER2 | | | |
| Negative | 131 (91.6) | 537 (84.3) | |
| Positive | 12 (8.4) | 100 (15.7) | 0.024 |
| Triple negative | | | |
| Non-TN | 130 (89) | 503 (80.5) | |
| TN | 16 (11) | 122 (19.5) | 0.015 |
| BRCA1 | | | |
| Negative | 43 (35.5) | 251 (47.8) | |
| Positive | 78 (64.5) | 274 (52.2) | 0.015 |
| MIB1 | | | |
| Negative | 63 (56.3) | 168 (32.2) | |
| Positive | 49 (43.8) | 355 (67.8) | <0.001 |
| EGFR | | | |
| Negative | 114 (90.5) | 448 (81) | |
| Positive | 12 (9.5) | 105 (19) | 0.011 |
| p63 | | | |
| Negative | 143 (98.6) | 611 (99.2) | |
| Positive | 2 (1.4) | 5 (0.8) | 0.519 |
| p53 | | | |
| Negative | 118 (83.1) | 425 (69.4) | |
| Positive | 24 (16.9) | 187 (30.6) | 0.001 |
| Cytokeratins | | | |
| CK 5/6 | | | |
| Negative | 125 (87.9) | 521 (85.1) | |
| Positive | 17 (12.1) | 92 (15) | 0.369 |
| CK 14 | | | |
| Negative | 132 (93) | 546 (89.8) | |
| Positive | 10 (7) | 62 (10.2) | 0.251 |
| CK 17 | | | |
| Negative | 112 (94.9) | 433 (85.7) | |
| Positive | 6 (5.1) | 72 (14.3) | 0.007 |
| CK 18 | | | |
| Negative | 18 (13.3) | 81 (14) | |
| Positive | 118 (86.8) | 497 (86) | 0.813 |
| CK 19 | | | |
| Negative | 11 (7.5) | 59 (9.5) | |
| Positive | 135 (92.5) | 565 (90.5) | 0.467 |

Pattern of ADA3 Expression in Breast Cancer Tissue Predicts Patient Outcome

Figure 3:
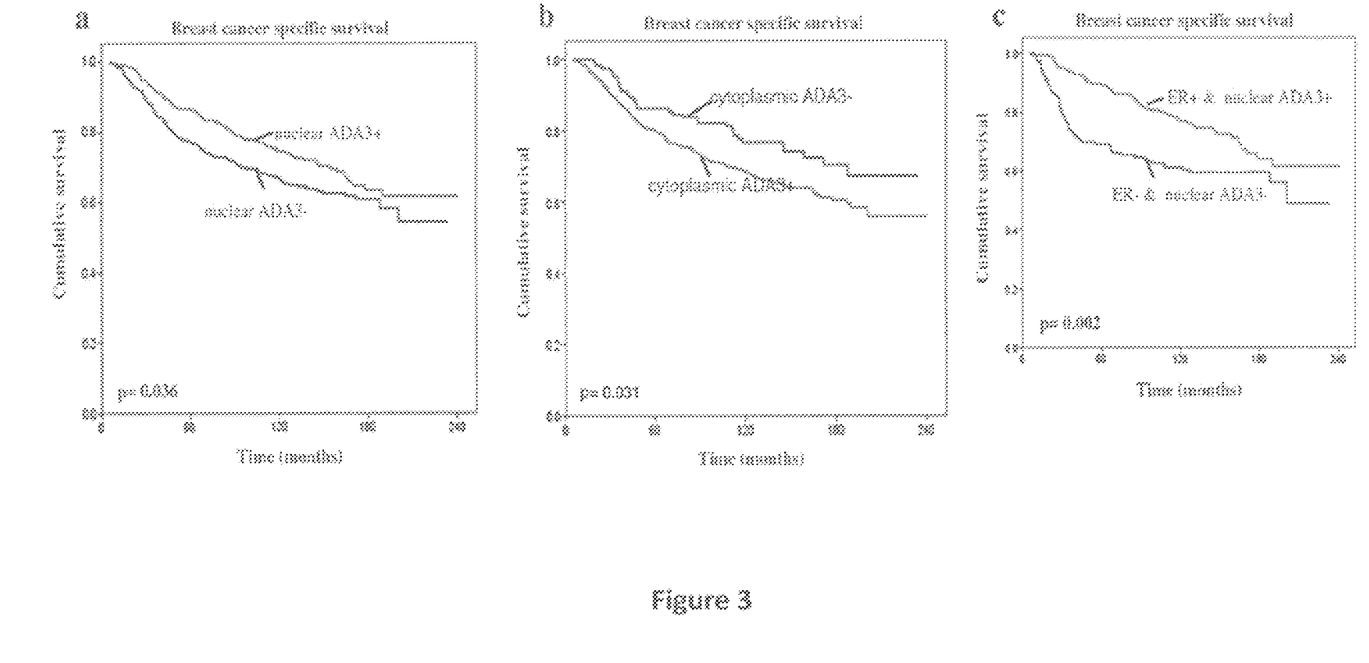

Next, it was assessed if ADA3 staining patterns could independently predict the patient outcomes. These analyses showed that tumors which lacked predominant nuclear ADA3 staining were associated with reduced BCSS (p=0.036) as compared to those showing nuclear ADA3 staining (FIG. 3A). Conversely, patients with predominant cytoplasmic ADA3 staining in breast tumor tissues showed reduced BCSS compared to those that did not show predominant cytoplasmic ADA3 staining (p=0.031) (FIG. 3B). Patients with negative nuclear ADA3 staining or positive cytoplasmic ADA3 staining in tumors showed a trend toward shorter DMFS; however, the association was not statistically significant (p=0.063 and p=0.050, respectively). Furthermore, multivariate analyses including other prognostic factors (i.e., grade, nodal status, size, and vascular invasion) showed that ADA3 was not an independent predictor of BCSS or DMFS.

Notably, combination of predominant nuclear ADA3 staining and ER+ status was associated with a better outcome as compared to patients whose tumors lacked nuclear ADA3 staining and were ER-negative (p=0.002 and p=0.014 for BCSS and DMFS, respectively) (FIGS. 3C, 3D). On the other hand, predominant cytoplasmic ADA3 staining in ER-negative tumors was associated with shorter survival time as compared to ER+ tumors that did not show predominant cytoplasmic ADA3 staining (p=0.002 and p=0.014, respectively) (FIGS. 3E, 3F).

Interestingly, analysis of the whole patient series revealed an association of predominant cytoplasmic ADA3 staining with shorter survival outcome among patients treated with hormone therapy (p=0.022 and p=0.036 for BCSS and DMFS, respectively), but not among patients that were not given hormone therapy. In contrast, the association of predominant nuclear ADA3 staining with a longer survival outcome was only seen in patients that did not receive hormone therapy (p=0.004 and p=0.007 for BCSS and DMFS, respectively).

Next, it was assessed if cytoplasmic expression of ADA3 predicts different outcomes in HER2/ErbB2+ and EGFR+ patients. These analyses revealed a significantly worse BCSS in HER2/ErbB2+ and EGFR+ patients that expressed high levels of cytoplasmic ADA3 (p=0.000, p=0.011, respectively) compared to those that did not overexpress cytoplasmic ADA3 (FIGS. 3G, 3H). Similarly, HER2/ErbB2+ patients and EGFR+ patients with high cytoplasmic ADA3 showed significantly reduced DMFS (p=0.000, p=0.0048, respectively) (FIGS. 3I, 3J). Due to a small number of patients (total 8-12) available in HER2+/EGFR+/cytoplasmic ADA3−, the correlation of this group with BCSS and DMFS was not assessed. Taken together, cytoplasmic ADA3 predicts poorer prognosis and outcome in HER2/ErbB2+ and EGFR+ patients. Taken together, these results show that the localization of ADA3 staining in tumor tissues predicts the survival outcomes among breast cancer patients.

Both clinicopathological markers and molecular classification have clearly indicated that breast cancer is a heterogeneous disease with distinct clinical outcomes (Sorlie et al. (2001) Proc. Natl. Acad. Sci., 98:10869-10874). While the existing predictive markers have vastly improved the ability to manage breast cancer patients and improved outcomes by matching therapeutic strategies with the types of breast cancer and existence of risk factors, it has also become evident that additional markers are needed to improve patient outcomes. Herein, ADA3 expression and subcellular localization in breast cancer was studied as a potential biomarker. Interest in ADA3 emanates from studies that have established the requirement of this evolutionarily conserved component of HAT coactivator complexes for transcriptional activation by ER and other nuclear hormone receptors as well as by other transcription factors (Meng et al. (2004) J. Biol. Chem., 279:54230-54240; Germaniuk-Kurowska et al. (2007) Cancer Res., 67:11789-11797; Nag et al. (2007) J. Biol. Chem., 282:8812-8820; Zeng et al. (2002) J. Biol. Chem., 277:45611-45618). As a known coactivator of ER-dependent transcriptional activation, investigation of ADA3 was of particular interest as 70-80% of breast cancers are ER+ and a large proportion of these patients respond to hormonal therapies targeting estrogen generation or response machinery (Howell et al. (2004) J. Clin. Oncol., 22:1605-1613; Dowsett et al. (2010) J. Clin. Oncol., 28:509-518; Johnson et al. (2012) Mol. Cell Endocrinol., 348:430-439). Furthermore, other studies have demonstrated that the expression of other ER coactivators such as SRC-3 correlates with disease outcome, including response to hormonal therapy (Johnson et al. (2012) Mol. Cell Endocrinol., 348:430-439). Here, it is shown that tumors frequently express predominant ADA3 either in the nucleus or cytoplasm, and that these discrete localizations correlate with ER positivity and HER2/ErbB2 overexpression, respectively. Importantly, nuclear ADA3 expression in ER+ breast cancers predicts more favorable clinical outcomes (BCSS & DMFS), while lack of nuclear ADA3 expression in ER+ tumors was associated with poorer outcomes. In contrast, cytoplasmic ADA3 expression in ErbB2/EGFR-overexpressing breast cancers was associated with a poorer outcome. Thus, the instant studies indicate that ADA3 expression and its nuclear vs. cytoplasmic compartmentalization in tumor cells serves as a prognostic marker to facilitate management of breast cancer patients.

To assess the expression of ADA3 in breast cancer, the ability of a mAb to specifically detect the expression of human ADA3 in an IHC format was established. By utilizing Ada3$^{fl/fl}$ versus Ada3-null MEFs, through conditional deletion of floxed Ada3 (Mohibi et al. (2012) J. Biol. Chem., 287:29442-56) and human mammary epithelial cells with ectopic overexpression of a FLAG-tagged ADA3 versus vector controls, the ability of the mAb anti-ADA3 to specifically detect ADA3 was established and an assessment of levels and localization of ADA3 expression in a cell-based IHC was provided.

Using TMAs generated from a large cohort of breast cancer tissue specimens with known clinicopathological parameters and survival data and a panel of normal breast tissues, it was first demonstrated that while basal level of both nuclear and cytoplasmic ADA3 was seen in breast duct epithelial cells, about 81% of breast cancer specimens showed prominent strong cytoplasmic ADA3 staining, either exclusively or together with nuclear staining, while 13% of tumors exhibited predominantly strong nuclear ADA3 staining.

The presence of five potential nuclear hormone binding LXXLL (SEQ ID NO: 1) motifs and a predicted nuclear localization signal (NLS) in ADA3 led to studies that demonstrated the role of ADA3 as a coactivator for ER and RXR (Meng et al. (2004) J. Biol. Chem., 279:54230-54240; Li et al. (2010) Nucleic Acids Res., 38:5291-5303). Interestingly, the well-known ER coactivator SRC-3 is known to undergo estrogen-induced phosphorylation in the cytoplasm followed by its transport to the nucleus (Zheng et al. (2005) Mol. Cell Biol., 25:8273-8284; Amazit et al. (2007) Mol. Cell Biol., 27:6913-6932), suggesting that phosphorylation of coactivators may determine their nuclear localization. Publicly available proteomics datasets indicate that ADA3 can undergo several post-translational modifications including phosphorylation, acetylation, methylation, and ubiquitination, all of which can affect subcellular localization of proteins. Potential structural alterations of the putative NLS or posttranslational modifications could alter ADA3 localization in breast cancer cells.

Notably, about 6% of breast cancer specimens analyzed showed undetectable ADA3 staining. In addition to altered post-translational modifications, discussed above in relation to localization, reduced ADA3 expression can be due to genetic and/or epigenetic alterations. Tumors having a reduction in ADA3 expression may have an activation of alternate pathways that compensate for ADA3 functions. Such compensation is suggested by studies with genetic knockout of ADA3: deletion of ADA3 in mouse germline induces early embryonic lethality and its conditional deletion in mouse embryonic fibroblasts induces cell cycle block (Mohibi et al. (2012) J. Biol. Chem., 287:29442-56). These findings indicate that loss of ADA3 in tumors might be compensated by upregulation of an alternate functional pathway since mammals do not possess a close structural homolog of ADA3. Furthermore, studies have demonstrated that a loss of ADA3 induces genomic instability and delay in DNA repair process (Mirza et al. (2012) Cell Cycle 11:4266-4274), underscoring the role of ADA3 in oncogenesis.

Although in multivariate analyses ADA3 expression was not an independent marker of survival; all ER-positive breast cancer specimens revealed the presence of nuclear ADA3 and predicted good prognosis as compared to breast cancers where ADA3 was cytoplasmic. Furthermore, nuclear staining of ADA3 was significantly associated with BRCA1 expression, which is a known tumor suppressor in breast cancer (Rosen et al. (2005) Endocr. Relat. Cancer 12:533-548; Miki et al. (1994) Science 266:66-71), and was significantly associated with cytokeratin 18, a luminal marker. Thus, predominant nuclear ADA3 expression is correlated with luminal ER+ breast cancers. Interestingly, nuclear SRC-3 expression also correlates with the luminal ER+ subtype of breast cancer (Osborne et al. (2003) J. Natl. Cancer Inst., 95:353-361).

Unexpectedly, predominant cytoplasmic ADA3 staining was seen in a substantial subset of breast cancers and correlated with higher tumor size, histological grade, MIB1 expression, increased mitotic count, positive vascular invasion, and higher NPI, all well-known markers associated with poor prognosis. Given the negative correlation of cytoplasmic ADA3 staining with ER+ status, it was determined if cytoplasmic ADA3 correlates with other biological markers that predict distinct outcomes. Significantly, cytoplasmic ADA3 staining was positively associated with overexpression of EGFR and ErbB2, markers that predict poor prognosis in breast cancer (Bailey et al. (2011) J. Carcinog., 10:28). Significantly, cytoplasmic ADA3 in the HER2/EGFR overexpressing patients predicted a poorer outcome both in terms of BCSS and DMFS. Thus, additional markers that might improve the prediction of outcomes in ErbB2-overexpressing subset of patients could help physicians and patients in deciding on options for treatment strategies.

Signaling pathways downstream of EGFR/ErbB2 may play a role in ADA3 localization, possibly through post-translational modifications of ADA3. Alternatively, cytoplasmic ADA3 may modify signaling downstream of EGFR/ErbB2. In this regard, an SRC-3 splice variant SRC-3Δ4 is known to promote EGF-induced phosphorylation of FAK and c-Src (Long et al. (2010) Mol. Cell 37:321-332). Furthermore, overexpression of SRC-3 together with the presence of EGFR/ErbB2 is associated with resistance to tamoxifen therapy and decreased disease-free survival (Arpino et al. (2008) Endocr. Rev., 29:217-233: Lahusen et al. (2009) Breast Cancer Res. Treat., 116:225-237).

In conclusion, the instant studies provide evidence that nuclear versus cytoplasmic ADA3 localization serves as a prognostic marker in breast cancer; while predominant nuclear ADA3 localization is associated with ER+ status and markers of good prognosis, predominant cytoplasmic localization is associated with markers of poor prognosis and correlates with EGFR+ and ErbB2+ breast cancer subtypes.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating breast cancer in a subject, said method comprising:
    a) determining the cellular localization of alteration/deficiency in activation-3 (ADA3) in a biological sample obtained from said subject, wherein said biological sample is a breast cancer tissue sample; and
    b) administering hormonal therapy to said subject when ADA3 is determined to be predominantly nuclear and administering human epidermal growth factor receptor 2 (HER2) targeted therapy when ADA3 is determined to be predominantly cytoplasmic or overexpressed, thereby treating the breast cancer in said subject.

2. The method of claim 1, wherein human epidermal growth factor receptor 2 (HER2) targeted therapy is administered when ADA3 is determined to be predominantly cytoplasmic.

3. The method of claim 1, further comprising detecting at least one other breast cancer marker in said biological sample.

4. The method of claim 3, wherein said other breast cancer marker is selected from the group consisting of estrogen receptor (ER), progesterone receptor (PR), HER2, and epidermal growth factor receptor (EGFR).

5. The method of claim 4, wherein the other breast cancer marker is ER and/or PR, and wherein said subject is administered hormonal therapy when ADA3 is determined to be predominantly nuclear and the biological sample is positive for ER and/or PR.

6. The method of claim 4, wherein the other breast cancer marker is HER2 and/or EGFR, and wherein said subject is administered HER2-targeted therapy when ADA3 is determined to be predominantly cytoplasmic and the biological sample is positive for HER2 and/or EGFR.

7. The method of claim 1, wherein said hormonal therapy comprises the administration of at least one estrogen receptor modulator or aromatase inhibitor.

8. The method of claim 1, wherein said HER2-targeted therapy comprises the administration of at least one inhibitor of HER2 or antibody immunologically specific for HER2.

9. The method of claim 8, wherein said or antibody immunologically specific for HER2 is trastuzumab.

10. The method of claim 1, further comprising the administration of at least one other chemotherapeutic agent.

11. The method of claim 1, further comprising treating the subject with radiation or resecting cancerous cells from said subject.

12. A method for treating breast cancer in a subject, said method comprising:
    a) determining the cellular localization of alteration/deficiency in activation-3 (ADA3) in a biological sample obtained from said subject, wherein said biological sample is a breast cancer tissue sample; and
    b) administering hormonal therapy to said subject when ADA3 is determined to be predominantly nuclear, thereby treating the breast cancer in said subject.

* * * * *